United States Patent [19]

Stratis et al.

[11] Patent Number: 4,978,749

[45] Date of Patent: Dec. 18, 1990

[54] NON-RADIOACTIVE LABELLED SINGLE-STRANDED PROBE, METHOD FOR MANUFACTURING IT AND METHOD FOR DETECTING A SPECIFIED NUCLEOTIDE SEQUENCE USING THIS PROBE

[75] Inventors: Avrameas Stratis, Paris; Hiroshi Sakamoto, Meudon; Francois Traincard, Paris; Tuyen Vo Quang, Paris; Jean-Luc Guesdon, Paris; Therese Ternynck, Paris, all of France

[73] Assignees: Institute Pasteur; Centre National De La Recherche Scientifique, both of Paris, France

[21] Appl. No.: 378,507

[22] Filed: Jul. 11, 1989

Related U.S. Application Data

[63] Continuation of Ser. No. 33,193, Apr. 2, 1987, abandoned.

[30] Foreign Application Priority Data

Apr. 4, 1986 [FR] France ................................ 86 04913

[51] Int. Cl.$^5$ ...................... C07H 21/04; C07H 5/02; C12Q 1/68; G01N 33/531; C12N 15/11
[52] U.S. Cl. .......................................... 536/27; 435/6; 435/7; 435/235; 435/239; 435/320; 436/501; 530/387; 536/27; 935/73; 935/78; 935/12; 935/110
[58] Field of Search ................... 435/6, 235, 239, 320, 435/7; 436/501; 530/387; 536/27; 935/73, 12, 78, 110

[56] References Cited

U.S. PATENT DOCUMENTS

| | | | |
|---|---|---|---|
| 4,529,700 | 7/1985 | Gratzner | 435/240 |
| 4,585,736 | 4/1986 | Dolbeare et al. | 435/6 |
| 4,687,732 | 8/1987 | Ward et al. | 435/6 |

FOREIGN PATENT DOCUMENTS

0143059 11/1984 European Pat. Off. .

OTHER PUBLICATIONS

Sakamoto et al. (1987) Molecular and Cellular Probes, vol. 1, pp. 109–120.
Traincard et al. (1983) Ann., Imnunol. (Inst. Pasteur), vol. 134D, pp. 399–405.
Gratzer, H. G. (1982) Science 218, pp. 474–475.
Stratis, A., et al., European Patent Application No. 0,143,059–Al, Filed 11/12/84.

*Primary Examiner*—Robert A. Wax
*Assistant Examiner*—Ardia Marschel
*Attorney, Agent, or Firm*—Finnegan, Henderson, Farabow, Garrett & Dunner

[57] ABSTRACT

The invention relates to a new probe for detecting a specified nucleic acid sequence. It consists of a recombinant DNA containing an insert complementary to the nucleic acid sequence to be detected and nuclecic acid sequences derived from the DNA (+) of phage M13, the bases which participate in the composition of this recombinant DNA, in particular the thymine groups, being replaced by 5-bromouracil groups. The invention also relates to a method for manufacturing this probe, this method comprising the culturing of cell hosts, more especially *E. coli,* which are auxotrophic for thymine in a medium containing a limiting concentration of thymine and containing 5-bromouracil. After the requisite incubation time, the supernatant is removed and the probe is recovered from the bacterial cells.

9 Claims, No Drawings

NON-RADIOACTIVE LABELLED SINGLE-STRANDED PROBE, METHOD FOR MANUFACTURING IT AND METHOD FOR DETECTING A SPECIFIED NUCLEOTIDE SEQUENCE USING THIS PROBE

This application is a continuation, of application Ser. No. 033,193, filed Apr. 2, 1987 now abandoned.

The invention relates to a single-stranded non-radioactive labelled specific probe, and to a method for detecting by hybridization the presence and, where appropriate, for the characterization of a specified nucleotide sequence within a composition containing nucleic acids. This non-radioactive labelled probe itself contains a nucleotide sequence complementary to the nucleotide sequence to be detected. The detection test consequently involves a hybridization reaction, under the appropriate conditions, between the complementary sequence carried by the probe and the specified nucleotide sequence to be detected, generally in the presence of nucleic acids other than those containing the sequence to be detected.

The invention also relates to a method for manufacturing such a non-radioactive probe.

Specific hybridization probes for detecting a specified nucleic acid sequence (DNA or RNA) were for a long time—and are frequently still—labelled with radioactive isotopes, permitting autoradiographic detection.

The main disadvantages of autoradiographic detection of hybridization are well known. They reside essentially in the dangers incurred by the experimenter when he handles radioactive products, the poor resolving power, the inaccuracy of the localization, the length of exposure time of the films (from a few hours to several weeks) and the instability of the probes due to radiolytic decomposition and to the duration inherent in the radioisotopes used.

To remedy this difficulty, it has already been proposed to replace radioactive labelling by other methods of labelling. The technique described for the first time in French Patent No. 78/10,975, filed on 13th April 1978, will be recalled in particular.

The method described in the patent referred to above employs a probe modified by coupling, or for the purpose of coupling it—directly or indirectly—with an enzyme, preferably subsequently to the hybridization reaction, the possible presence of the nucleic acid sequence or the nucleic acid sought then being capable of visualization by means of the action of the product of coupling the enzyme and the probe (the latter then being hybridized with the nucleic acid sequence sought) on a substrate for the enzyme. By way of example of an enzyme which is commonly used, beta-galactosidase, glucose oxidase, alkaline phosphatase and peroxydases will be mentioned. As a variant, the detection or "visualization" of the hybridized probe can employ means other than an enzyme, for example immunofluorescence techniques.

To accomplish the modification of the probe for the purpose of subsequently coupling it with an enzyme or an immunofluorescent molecule, increasing use is being made of the incorporation into the nucleic acid of the probe of nucleotides bearing haptens capable of being recognized by specified antibodies. The actual detection operation then frequently involves a sequence of reactions comprising a first step of bringing the hybridized probe bearing the haptens into contact with the anti-hapten antibodies, followed by a second step of bringing the hybridized probe, which then carries anti-hapten antibodies, into contact with immunoglobulins or other molecules having affinity directed against these antibodies, these immunoglobulins themselves bearing a non-radioactive label, for example an enzymatic or fluorescent label. There is no need to dwell on the conditions under which these techniques can be carried out. Reference may be made, for example, to European Patent Application No. 0,063,869-A3, in which several of these techniques are described.

The techniques which have just been recalled, both of which employ non-radioactive probes or, for convenience of expression hereinafter, "cold probes" (in distinction to the "hot probes" represented by the probes labelled with radioactive isotopes), possess considerable advantages compared with the "hot probes", if only in respect of the greater safety of the experimenters who use them. However, it is also still necessary to improve the probes themselves, to make them both more efficient and more sensitive, on the one hand, as well as the methods for manufacturing them, in order to reduce the cost of these probes.

In an effort to attain these objectives, it has already been proposed, in particular in European Patent Application No. 0,063,869-A3, already mentioned, and in European Patent Application No. 0,143,059-A1 filed on 23rd November 1984, to modify a part of the bases present in one of the constituent nucleotides of the probe by substitution groups of small molecular size, in particular in the 5-position when the base is a pyrimidine and in the 7-position or 8-position, or in both positions at once, when the base is a deazapurine or purine.

In general, it is possible to use any modified base which does not interfere with the capacity of the nucleic acid thus modified to undergo WATSON-CRICK pairing with a natural complementary nucleic acid or one containing similar modified bases. However, the preferred probes are those in which the modified nucleosides are 5-halouridine or 5-halodeoxyuridine groups, and still more especially those in which the modified nucleosides are 5-bromouridine or 5-bromodeoxyuridine groups. Other preferred groups capable of being employed in the context of this invention involve corresponding derivatives substituted with iodine or fluorine, or alternatively with $CF_3$ groups.

These cold probes can then, after hybridization, be detected by means of antibodies, preferably monoclonal antibodies selectively directed against the halogenated bases.

European Patent Application No. 0,143,059-A1, mentioned above, also describes a method for manufacturing in vivo probes of the type defined above in microorganisms, in particular bacteria, and more especially E. coli, starting with a recombinant DNA or a vector DNA capable of transforming a microorganism, such as a plasmid, cosmid or phage DNA, in Which the nucleotide sequence (hereinafter referred to as insert) complementary to the nucleic acid sequence to be detected had been inserted beforehand. This method comprises the setting up and maintenance in culture of the microorganism, previously transformed by this recombinant DNA, with a culture medium containing the modified base replacing the corresponding natural base, the abovementioned modified base being present therein either in the free state, or in the combined state in a nucleoside or nucleotide corresponding to the said base, and the subsequent recovery of the recombinant DNA or vector DNA.

This method then permits the in vivo substitution of at least one of the bases present within these recombinant DNAs and vector DNAs, inside the microorganism itself which is maintained in culture in the medium containing the modified base.

The objective of the present invention is to obtain still more efficient recombinant cold probes, possessing a degree of sensitivity, in respect of detection, which has never yet been achieved with this type of probe labelled in vivo.

Its objective is also an especially simple method for manufacturing these probes in vivo, after transformation of a suitable microorganism, in particular E. coli, with a recombinant vector containing an insert specific for the nucleotide sequence to be detected.

The invention rests on a particular choice of DNA sequences which, in combination with the specific insert, will form the cold probe which is more especially described and claimed below.

The recombinant probe according to the invention is characterized:

by its single-stranded nature, having single polarity and being incapable of self-hybridization, by the combination of the insert, specific for the nucleotide sequence to be detected, with heterologous strands possessing nucleotide sequences present in the DNA of a single-stranded phage whose infectious biological cycle, with respect to the competent cell host, normally involves the production of an intracellular double-stranded template retained inside the cell host and the excretion of the single replication strand, in particular in encapsidated form, into the culture medium of the competent microorganism, and by a modification group on the base of one of the constituent nucleotides of the probe assembly, the modification comprising a halogenated substitution group and this substitution being to the extent of more than 60% and preferably to the extent of all the nucleotides in question in the said probe, the said modification rendering the probe capable of recognition by specific antibodies which themselves recognize this modification group.

Advantageously, the strands combined with the insertion sequence correspond to single-stranded DNA sequences present in the genome of a phage which is infectious with respect to E. coli, of the type which is known under the designation M13 according to the definition thereof given, for example, in French Patent No. 82/18,469-2,516,094.

The method according to the invention for producing the abovementioned recombinant probe is of the type which comprises a stage of infection of a competent cell host with a vector containing the specific probe insert in one of its regions which are nonessential in relation to its capacity for replication in this cell host, a stage of propagation of the cell host in a suitable culture medium and a stage of recovery of the probe.

The method according to the invention is more especially characterized by the combination of the following characteristics:

the vector is a phage chosen from single-stranded phages whose infectious biological cycle with respect to the corresponding competent cell host normally involves the production of an intracellular double-stranded template retained inside the cell host and the excretion of the replicated single strands, in particular in encapsidated forms, into the culture medium, the cell host is auxotrophic for the natural base which participates in the composition of one of the four natural nucleotides, the medium in which the propagation of the cell host is carried out has a limiting concentration of the said natural base, the medium also contains, at least at the time when the natural base has been completely consumed, a concentration of a base corresponding to the said base, this base being, however, modified by a halogenated group, the culture is maintained, from the time when the natural base has been completely consumed, for a sufficient period to provide for the excretion of the unmodified replicated viral DNA into the culture medium and also the accumulation of the modified replicated viral DNA in the cell host, and the cell host is then recovered and the single-stranded viral DNA containing the modified bases is then extracted from it.

When a viral vector of the M13 type is used, the preferred competent cell host consists of an E. coli which is auxotrophic for one of the four bases which participates in the composition of nucleotides, preferably for thymine.

The halogenated modification group, to which reference is made in the definitions of the probe and the method according to the invention, consists of any group of this type which does not interfere with the capacity of the modified vector for being recognized by the polymerases of the competent cell host and, subsequently, with the capacity of the probe to hybridize with the nucleic acid sequence sought. Modified nucleosides which participate in the composition of the probes according to the invention, can be those which have been mentioned above in connection with the invention described in European Patent Application No. 0,143,059-A1.

As regards, more especially, the method according to the invention, the modified base used in the corresponding stage can consist either of the base itself in the free state, or in the combined state in the nucleoside or nucleotide corresponding to the said base. Preferably, the modification concerns the thymine bases. The corresponding nucleosides in the probe advantageously consist of 5-halouridine or 5-halodeoxyuridine groups, and still more especially those in which these modified bases are 5-bromouridine or 5-bromodeoxyuridine groups.

The cold probes according to the invention have the feature of being single-stranded, having single polarity and being incapable of self-hybridization. These characteristics are of value considering the very great sensitivity of detection which can be achieved with these probes. In addition, the single-stranded nature provides for optimum access to the molecules having affinity, in particular monoclonal antibodies which recognize the modified bases. This observation applies especially to monoclonal antibodies capable of recognizing brominated bases, such as 5-halouracil, and more especially 5-bromouracil, groups.

The particular advantage of the selection of the vector used, among the many vectors which are usable, resides in the discovery, made by the inventors, that the modification of some of the bases in the products of replication of the genomic DNA of the phages in question inside the corresponding cell hosts rendered them incapable of crossing the cell membranes of the host, in contrast to what is observed with the corresponding unmodified replicated DNAs obtained from the same phages. This characteristic manifests itself in several specific advantages.

It enables the unmodified replicated DNAs (excreted into the culture medium) and the modified replicated DNAs, retained within the cell host, to be separated within the cell host itself. In addition, especially as a result of suitable adjustment of the conditions of the method of manufacture, it is possible to achieve complete substitution of the base in question in the replicated DNAs by the corresponding modified base. Finally, these modified single-stranded DNAs, containing the insertion sequence characteristic of the probe, can be obtained from the cell host previously separated from the culture medium. After rupture of the bacterial walls, the modified probe is directly accessible by purification methods of the type applicable to the separation, for example by differential centrifugation in a suitable gradient, of plasmids from cytoplasmic extracts of the cells which harbour them. It will be noted that these modified phages, containing the specific insertion sequence of the probe, are obtained directly in the single-stranded state, in the absence of any encapsidation protein. Hence, it follows from the foregoing that the main difference between the traditional procedure for recovering the replicated DNAs of phages of the type in question and the method of the invention resides in the fact that, in the first case, the replicated DNA is obtained from the supernatant (the single-stranded DNA then generally being in the encapsidated state) whereas, in the case of the method according to the invention, the modified DNA containing the insertion sequence is obtained from the cell hosts themselves.

As has been stated above, the preferred competent cell host, in this instance E. coli when a phage of the M13 or similar type is used, is auxotrophic for one of the four bases, for example thymine, which participates in the composition of nucleotides, and the medium in which the propagation of the cell host is carried out has a limiting concentration of the corresponding natural base.

The expression "limiting concentration" should be understood in this context to mean an initial concentration of natural bases, for example thymine, which is less than the concentration of the natural base capable of being absorbed by the transformed cell culture to attain its maximum development. In other words, this limiting concentration has the effect of blocking the growth of the culture at a level below its maximum capacity for growth, as a result of the auxotrophy of the cells of which it is composed with respect to the natural base. However, if the culture medium also contains the corresponding modified base at the time when the concentration of natural base becomes exhausted, cellular activity continues, even though the culture no longer tends to grow, this occurring in the presence of the corresponding modified base. In this post-growth phase, the viral DNAs containing the modified base, and which will subsequently constitute the probes according to the invention, are then produced. During this cellular activity, the replicated DNAs still formed with the natural base are excreted into the culture medium, while the replicated viral DNAs formed with the modified base remain trapped inside envelopes defined by the cell membranes.

Advantageously, the limiting concentration corresponds to the concentration of natural bases which corresponds to that which is required for attaining the maximum rate of growth of culture per unit time. At this point, the cell activity is then at a maximum, and its consequence is the production of large amounts of replicated viral DNAs containing the said modified bases by the cells which, however, cease to divide as a result of the disappearance of the natural base.

E. coli mutants which are auxotrophic for thymine can be selected in the presence of trimethoprim, according to the technique described by Miller et al, 1972, "Experiments in Molecular Genetics", Cold Spring Harbor Laboratory, or alternatively according to the procedure described by Stacey K. A. et al, (1965), J. Bact. 90, 554–555.

It is naturally possible to use other types of modified bases, for example 5-bromocytosine, 8-bromo-guanine and 8-bromoadenine. Reference will, however, be made to European Patent Application No. 0,143,059-A1, as regards the further constraints with which the E. coli mutants used must comply. These mutants will also have to contain for example, mutations in the genes coding for ribonucleoside-diphosphate reductase (EC 1.17.4.1), in particular at the nrdA and nrdB loci (Bachmann et al, 1980, Microbiological Reviews, 44:1–56).

It will be understood that the modified base can be present in the culture medium from the outset, or added at any point to the culture medium before its concentration of natural bases has become exhausted.

The above combination of operations can also be carried out shielded from radiation having wavelengths shorter than 400 nanometers (this radiation being capable of causing the loss of halogen in the case of nucleic acids modified by 5-halouracil groups). In particular, the in vivo and in vitro preparation of the probes according to the invention can be carried out in darkness or in light consisting of radiation having wavelengths longer than 400 nanometers. The introduction of an inert dye into the culture medium of the hosts transformed by the vector carrying the nucleic acid (insert) intended for the preparation of a probe, the dye being non-toxic for the host and the vector and absorbing in wavelengths shorter than 400 nanometers, can constitute a means of escaping from the constraint which might, in some cases, be imposed by the above restrictions regarding the nature of the light to be used.

The probes according to the invention can be stored in the lyophilized state in any suitable vessel or on any suitable support. They can also be stored in bottles or vessels made of a material which absorbs in wavelengths shorter than 400 nanometers. The probes according to the invention can also be stored in the state of solutions, either in a vessel which complies with the above-mentioned conditions or in vessels whose walls are not absorbing, in which case these solutions themselves contain an inert dye which absorbs in wavelengths shorter than 400 nm.

Further characteristics of the invention will also emerge in the course of the description which follows of an example of production of a single-stranded cold probe according to the invention, it being understood that this description cannot be interpreted as being limiting in nature as regards the scope of the claims of the present patent application.

EXAMPLE

The phage used consists of bacteriophage M13. It is identical to that present in the transformed E. coli micro-organism (JM103(W14)) which was described in French Patent Application No. 82/18,469-2,516,094. Such a phage is, for example, accessible in the "National Collection of Industrial Bacteria" (NCIB) of the Torry Research Station, Aberdeen, Scotland. It was deposited on 12th November 1981. It has received the accession number 11,704.

The strain JM103 (described in the publication by Maniatis T. et al, Cold Spring Harbor, 1982) was also used as the parent strain in the context of the invention. Selection of a strain auxotrophic for thymine was carried out under the conditions recorded above. The selected clone, designated TUC0701, was shown to be a thymine-dependent mutant requiring at least 50 micrograms/milliliter of thymine for optimal growth in mucoid-free liquid synthetic medium permitting the growth of bacteriophage M13. This strain was deposited in the Collection Nationale de Culture de Microorganismes (CNCM) (National Collection of Microorganism Cultures) of the Institut Pasteur of Paris on 3rd April 1986. It was assigned the following deposition number: I-541.

This strain was used for incorporating 5-bromo-deoxyuridine in vivo into the DNA of bacteriophage M13 which had previously been modified, in one of its regions which are nonessential for its replication, by a specific nucleotide insert complementary to the nucleotide sequence to be detected. Such a modified probe can be produced by employing the separation procedure described below for the labelling of the DNA (more especially, the +strand of the DNA) of phage M13.

2 ml of preculture of the strain TUC0701 were prepared. The latter was cultured at 37° C. overnight in M9 synthetic medium supplemented with thymine to attain a final concentration of 0.1 mg/ml.

2 ml of a bacteriophage M13 stock are added to the medium.

The mixture is incubated for 15 minutes at 37° C. in the absence of agitation.

100 ml of nutrient-rich medium are then added: 2 x YT to which 5-bromouracil has been added to the extent of 0.3 mg/ml final.

Culturing is performed at 37° C. with vigorous agitation, if required with oxygenation using compressed air and adjustment of the pH to the value 7.

The growth curve of the culture is observed (by measuring the increase in the optical density at 600 nanometers). The bacteria are harvested 2 hours after the beginning of the stationary phase. The supernatant, possibly containing encapsidated viral DNAs, is discarded.

When the above-mentioned separation is carried out by centrifugation, the bacterial pellet constitutes, as a result, the starting material for the subsequent extraction of the probe. In particular, after lysis of the bacteria, the extrachromosomal DNA is extracted and purified by the so-called fast protein liquid chromatography method, known by the abbreviation FPLC, for example according to the method described by Vo-Quang T. et al, Bioscience Reports (1985) 5, 101–111 or by any other suitable technique, for example according to the technique of Maniatis T. et al, "Molecular Cloning", Cold Spring Harbor Laboratory 1982.

The replicated phage M13 DNA, modified by the 5-bromouracil groups, can, when it also contains the above-mentioned specific insert, be directly used as a probe, since it is already freed from the phage capsid. It must already be in the single-stranded state to the extent of at least 90% (the proportion of double-stranded labelled probe is measurable after treatment of the labelled probe with S1 nuclease) (Maniatis et al).

The technique described above permits very high production yields: at least 10 micrograms of labelled probe per milliliter of bacterial culture, equivalent to a yield of the same order of magnitude as that obtained in the conventional procedures for extraction of unlabelled single-stranded DNA from bacteriophage M13, in particular under the conditions described by the company which markets it: Amersham "M13 Cloning and Sequencing Kit".

The labelled probes obtained are characterized by a very great sensitivity. The threshold of detection, tested by the so-called dot test method described by Traincard F. et al Ann. Immuno. Inst. Pasteur (1983) 134 D 339–405, is at 1 pg of deposited probe (visualization by peroxidase/diaminobenzidine).

The probes obtained can be used in any manner known per se. If the dot hybridization technique described by Traincard F. et al, already mentioned, is used, it is found that the probes according to the invention enable one pg of target DNA deposited on a membrane to be detected, it being understood that the expression (target DNA) refers to a DNA complementary to the probe (visualization by alkaline phosphatase/bromochloroindolyl phosphate/nitro blue tetrazolium).

Probes obtained are uniformly and completely labelled. This result could be achieved in the context of the prior techniques only in much more complex labelling systems.

The culture media M9 and 2 x TY are described in the instructions published by Amersham already mentioned (M13 Cloning and Sequencing Kit).

It is naturally self-evident that the invention relates to all possible variants. It has been described more especially in relation to phage M13. It goes without saying that it can be applied, under similar conditions, with other phages which comply with the conditions which have been defined above. By way of example of other phages which can be used under similar conditions, that known under the designation 4X174 will be used.

The probes thereby modified can be used in tests for detection by hybridization under conventional conditions. Advantageously, the detection comprises, subsequent to the hybridization operation, a stage of recognition of the hybridized probe by means of monoclonal antibodies directed against the modified base.

As regards the techniques, reference may be made, by way of examples, to the description in European Patent Application No. 0,143,059-A1.

It is self-evident that the various publications and patent applications which have been mentioned in the context of the present description must be considered to form part thereof, since the precise details which they contain may serve to clarify the meaning of some of the characteristic features of the present invention.

We claim:

1. A recombinant probe comprising a single-stranded nucleic acid having a single polarity and
    (a) a first nucleotide sequence for hybridization with another nucleotide sequence that is to be detected, and
    (b) a second nucleotide sequence that comprises a nucleotide sequence of a single-stranded phage, wherein said recombinant probe comprises a plurality of a modified base, said modified base comprising a corresponding natural base modified by a halogenated substituent, and wherein the number of said modified bases in said nucleic acid constitutes more than 60% of the sum of the modified bases and said corresponding natural base, and wherein said nucleic acid is capable of replication in a host cell, and capable of existing in a double-stranded form during replication in the host cell, and said double-stranded form is incapable of being excreted outside the host cell.

2. A recombinant probe as claimed in claim 1, wherein all of said corresponding natural base in the nucleic acid is modified by the halogenated substituent.

3. A recombinant probe as claimed in claim 1, wherein said phage is M13.

4. A recombinant probe as claimed in claim 1, wherein said phage is $\phi$x174.

5. A recombinant probe as claimed in claim 1, wherein said corresponding natural base is thymine and said modified base is 5-bromouracil.

6. A recombinant probe as claimed in claim 1, wherein said host cell is E. coli.

7. A recombinant probe as claimed in claim 1, wherein said probe is capable of reacting immunologically with monoclonal antibodies directed to said modified base.

8. A recombinant probe as claimed in claim 1, wherein said first nucleotide sequence is an insert in a region of the second nucleotide sequence, and wherein said region is not essential for replication of the recombinant probe in the host cell.

9. A recombinant probe as claimed in claim 1, wherein said host cell is auxotrophic for said corresponding natural base.

* * * * *

UNITED STATES PATENT AND TRADEMARK OFFICE
CERTIFICATE OF CORRECTION

PATENT NO. : 4,978,749

DATED : December 18, 1990

INVENTOR(S) : Stratis Avrameas, Hiroshi Sakamoto, Francois Traincard, Tuyen Vo Quang, Jean-Luc Guesdon, and Therese Ternynck It is certified that error appears in the above-identified patent and that said Letters Patent is hereby corrected as shown below:

TITLE PAGE: Item [19] line 2, change "Stratis et al." to --Avrameas et al.--; and Item [75] line 8, change "Avrameas Stratis" to --Stratis Avrameas--.

Signed and Sealed this

Seventh Day of July, 1992

Attest:

DOUGLAS B. COMER

*Attesting Officer*     Acting Commissioner of Patents and Trademarks